United States Patent
Xiao et al.

(10) Patent No.: US 11,583,383 B2
(45) Date of Patent: Feb. 21, 2023

(54) LUMINAL STENT

(71) Applicant: Lifetech Scientific (Shenzhen) Co., Ltd., Shenzhen (CN)

(72) Inventors: Benhao Xiao, Shenzhen (CN); Zonglin Liu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 148 days.

(21) Appl. No.: 16/473,885

(22) PCT Filed: Dec. 6, 2017

(86) PCT No.: PCT/CN2017/114802
§ 371 (c)(1),
(2) Date: Jun. 26, 2019

(87) PCT Pub. No.: WO2018/121197
PCT Pub. Date: Jul. 5, 2018

(65) Prior Publication Data
US 2020/0383769 A1   Dec. 10, 2020

(30) Foreign Application Priority Data
Dec. 28, 2016 (CN) .......................... 201611238319.3

(51) Int. Cl.
*A61F 2/07* (2013.01)

(52) U.S. Cl.
CPC .......... *A61F 2/07* (2013.01); *A61F 2002/077* (2013.01); *A61F 2250/0039* (2013.01); *A61F 2250/0069* (2013.01)

(58) Field of Classification Search
CPC ........ A61F 2/07; A61F 2002/077; A61F 2/06; A61F 2002/061; A61F 2/064;
(Continued)

(56) References Cited

U.S. PATENT DOCUMENTS 5,354,308 A * 10/1994 Simon ...................... A61F 2/90
606/198
6,273,910 B1 * 8/2001 Limon ...................... A61F 2/91
623/1.15
(Continued)

FOREIGN PATENT DOCUMENTS

AU    2007281553 B2    9/2013

OTHER PUBLICATIONS

International Search Report dated Mar. 7, 2018 for corresponding PCT Application No. PCT/CN2017/114802.
(Continued)

*Primary Examiner* — Jennifer Dieterle
*Assistant Examiner* — Rebecca Lynee Zimmerman
(74) *Attorney, Agent, or Firm* — Raymond Sun

(57) ABSTRACT

A luminal stent includes a tube body that can be compressed and expanded in the radial direction, and an anti-leakage structure. The tube body is divided by the anti-leakage structure into a first tube body positioned on one side of the anti-leakage structure, and a second tube body positioned on the other side of the anti-leakage structure, with at least part of the first tube body being encircled by the anti-leakage structure. In a compressed state, the maximum compression diameter of the anti-leakage structure and the first tube body encircled by the anti-leakage structure is greater than or equal to the maximum compression diameter of the second tube body.

19 Claims, 4 Drawing Sheets

(58) Field of Classification Search
CPC ........ A61F 2002/065; A61F 2250/0039; A61F 2250/0069; A61F 2250/0018; A61F 2002/072; B21F 45/008
See application file for complete search history.

(56) References Cited

U.S. PATENT DOCUMENTS

| | | | |
|---|---|---|---|
| 9,138,335 | B2 | 9/2015 | Cartledge |
| 10,624,768 | B2 | 4/2020 | Xiao et al. |
| 10,702,370 | B2 | 7/2020 | Shu et al. |
| 2003/0236567 | A1 | 12/2003 | Elliot |
| 2004/0148005 | A1* | 7/2004 | Heuser ............... A61F 2/915 623/1.11 |
| 2004/0254636 | A1* | 12/2004 | Flagle ............... A61F 2/2412 623/1.36 |
| 2010/0121424 | A1 | 5/2010 | Kubena et al. |
| 2011/0270378 | A1* | 11/2011 | Bruszewski ............ A61F 2/07 623/1.15 |
| 2012/0179236 | A1* | 7/2012 | Benary ............... A61F 2/07 623/1.13 |
| 2015/0100114 | A1* | 4/2015 | Shahriari ............ A61F 2/2418 623/1.13 |
| 2016/0367364 | A1* | 12/2016 | Torrianni ............ A61F 2/2436 |

OTHER PUBLICATIONS

Search report dated Jun. 26, 2020 for corresponding European Application No. EP 17 88 9447.
Office Action dated Nov. 12, 2019 for corresponding China Application No. 2017800026060.
Office Action dated Jul. 8, 2021 for corresponding India Application No. 201917028586.

* cited by examiner

LUMINAL STENT

FIELD

The present application relates to a cardiovascular medical device, and more particularly relates to a luminal stent.

BACKGROUND

In intravascular interventional therapy, both a fenestration technology and a parallel stent technology are used to solve the problem of blood supply to branch vessels.

The fenestration technology as shown in FIG. 1 is taken as an example. Type-III endoleak may possibly occur between a side hole of a large stent 1 and a branch stent 2 because of poor adherence of the branch stent 2 to the side hole. To solve the endoleak problem, a branch stent 2 having an anti-leakage structure, such as a skirt, is generally used, and the anti-leakage structure is used to enhance the sealing effect. As shown in FIG. 2 and FIG. 3, the branch stent 2 having a skirt 3 is correspondingly required to be delivered by a sheath having a relatively large diameter D. Furthermore, as the skirt 3 exists, and the diameters of all parts of the sheath are equal in an axial direction, a part 21 that is covered by the skirt 3 of the branch stent 2 and assembled into the sheath 4 would be pressed more closely onto a sheath core by the sheath, but a part 22 that is not covered by the skirt 3 would expand by itself to squeeze the sheath core 5 slightly and even form a gap from the sheath core 5. During the release, the part 22 not covered by the skirt 3 and the sheath core 5 may slide relative to each other, thereby leading to the displacement of the stent.

SUMMARY

For the shortcomings in the prior art, the present application provides a luminal stent which adapts to a relatively thin sheath and does not move during the release process.

One technical solution adopted by the present application to solve the technical problems is to provide a luminal stent having a tube body which can be compressed and expanded in a radial direction, and an anti-leakage structure connected with the tube body. The tube body is divided by the anti-leakage structure into a first tube body located on one side of the anti-leakage structure and a second tube body located on the other side of the anti-leakage structure. At least part of the first tube body is encircled by the anti-leakage structure. In a compressed state, the second tube body and the anti-leakage structure together with the first tube body encircled by the anti-leakage structure have maximum compression diameters when compressed to the extreme limit by a radial force distributed uniformly along a circumferential direction of the luminal stent. The maximum compression diameters of the anti-leakage structure and the first tube body encircled by the anti-leakage structure are approximately equal to the maximum compression diameter of the second tube body.

In one embodiment of the present application, the absolute value of the difference between the maximum compression diameters of the anti-leakage structure together with the part encircled by the anti-leakage structure of the first tube body and the maximum compression diameter of the second tube body is no more than 0.1 mm.

In one embodiment of the present application, the second tube body includes a tapered section connected with the first tube body and a straight barrel section connected with the tapered section. The diameter of the straight barrel section is greater than that of the part encircled by the anti-leakage structure of the first tube body.

In one embodiment of the present application, the difference between the diameter of the straight barrel section and the diameter of the part encircled by the anti-leakage structure of the first tube body is no more than 8 mm.

In one embodiment of the present application, the ratio of the difference between the diameter of the straight barrel section and the diameter of the part encircled by the anti-leakage structure of the first tube body to the diameter of the straight barrel section is 0.1-0.2.

In one embodiment of the present application, the axial length of the tapered section is 5 to 10 mm.

In one embodiment of the present application, the part encircled by the anti-leakage structure of the first tube body has a first diameter; and the part not encircled by the anti-leakage structure of the first tube body has a second diameter. The second diameter is unequal to the first diameter. The second diameter is greater than the first diameter.

In one embodiment of the present application, the anti-leakage structure includes an outer-layer coating membrane and an outer-layer radial supporting structure connected with the outer-layer coating membrane.

In one embodiment of the present application, the anti-leakage structure has an open end and a closed end. The closed end is located at a joint of the first tube body and the second tube body.

In one embodiment of the present application, the first tube body includes a first coating membrane and a first radial supporting structure connected with the first coating membrane. The second tube body includes a second coating membrane connected with the first coating membrane and a second radial supporting structure connected with the second coating membrane. The thickness of the first coating membrane is less than that of the second coating membrane, and/or, the metal coverage rate of the first radial supporting structure is greater than that of the second radial supporting structure.

In one embodiment of the present application, the first radial supporting structure includes multiple first waveform ring-like objects arrayed in sequence, and the second radial supporting structure includes multiple second waveform ring-like objects arrayed in sequence. The wire diameter of each first waveform ring-like object is less than that of each second waveform ring-like object, and/or, the number of wave crests of each first waveform ring-like object is less than that of wave crests of each second waveform ring-like object.

In one embodiment of the present application, the ratio of the thickness of the second coating membrane to the thickness of the first coating membrane is 1.2-4.5.

In one embodiment of the present application, the ratio of the wire diameter of each second waveform ring-like object to the wire diameter of each first waveform ring-like object is 2.0-5.0.

In one embodiment of the present application, a ratio of the number of the wave crests of each second waveform ring-like object to the number of the wave crests of each first waveform ring-like object is 4-23.

The diameter of the second tube body of the luminal stent of the present application is greater than that of the first tube body, so that the second tube body is in closer contact with the sheath core after the luminal stent is compressed into the sheath. Furthermore, after compression, the maximum compression diameter of the second tube body is approximately equal to that of the first tube body encircled by a skirt, so that a contact force of the luminal stent with the sheath core in the sheath is more uniform, which may prevent the luminal stent from sliding in the release process and avoid the risk caused by the displacement of the luminal stent.

BRIEF DESCRIPTION OF THE DRAWINGS

The present application will be further described below in combination with accompanying the drawings and embodiments. In the drawings.

DETAILED DESCRIPTION OF THE INVENTION

To understand the technical features, objectives and effects of the present application more clearly, specific implementation modes of the present application are described in detail now in combination with the accompanying drawings.

First Embodiment

Figure 1:
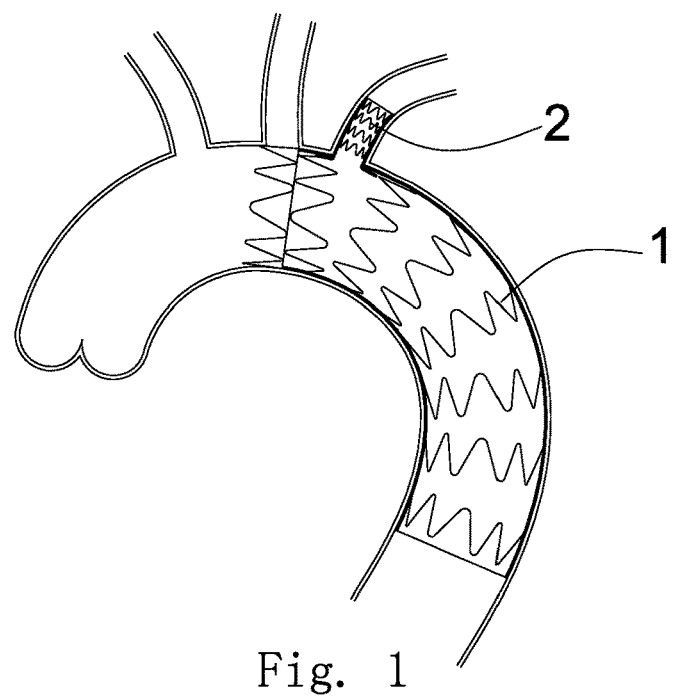
FIG. 1 is a structural schematic diagram of a luminal stent system in the prior art.
Figure 2:
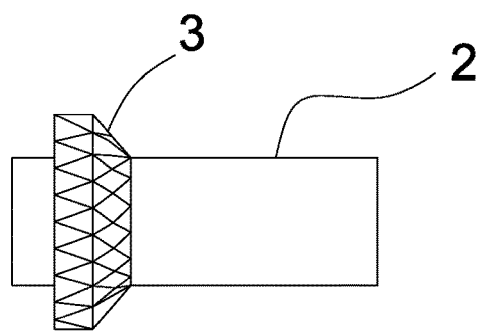
FIG. 2 is a structural schematic diagram of a branch stent of the luminal stent system in the prior art shown in an expanded state.
Figure 3:
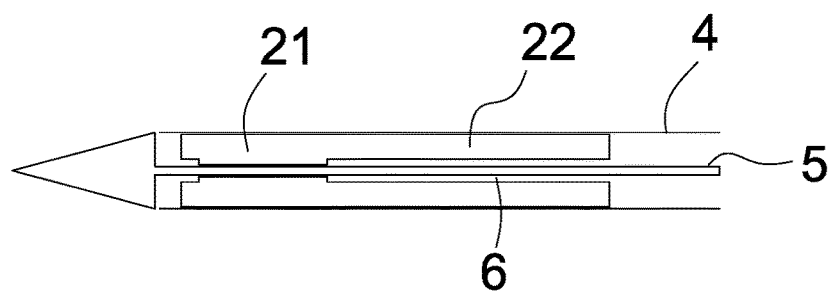
FIG. 3 is a structural schematic diagram of the branch stent in a compressed state in a sheath in the luminal stent system in the prior art.
Figure 4:
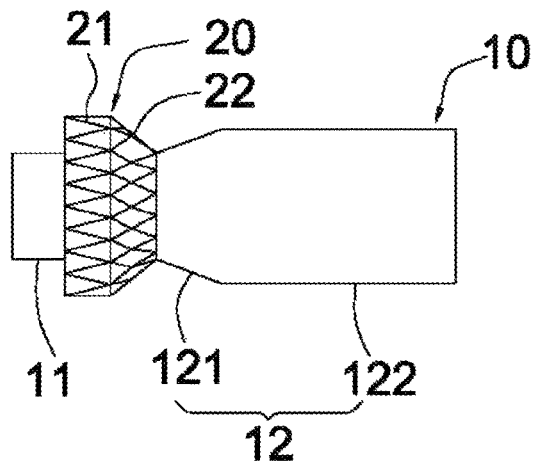
FIG. 4 is a structural schematic diagram of a first embodiment of a luminal stent of the present application shown in an expanded state.

As shown in FIG. 4, a luminal stent includes a straight barrel shaped tube body 10 and an anti-leakage structure arranged around the tube body 10 and connected with the tube body 10. The tube body 10 is of a membrane-coated stent structure having a radial supporting structure (not shown in the figure) and a coating membrane (not shown in the figure) covering the radial supporting structure. The radial supporting structure may be made of metal or other materials, such as stainless steel, a shape memory alloy, a titanium alloy or a polymer. The radical supporting structure includes multiple waveform ring-like objects (not shown in the figure) uniformly arrayed along the axial direction of the stent. The coating membrane is a biocompatible thin film made of polytetrafluoroethylene or terylene commonly used in this field. The self-expandable hollow columnar tube body 10 may be compressed and may expand in its radial direction. FIG. 4 is the structural schematic diagram of the tube body in its expanded state.

In the present embodiment, the anti-leakage structure is a skirt 20. In other embodiments, the anti-leakage structure may also have a capsular structure or a water-absorbing "fluffy" structure. The capsular structure is filled with a gel-like substance. The "fluffy" structure may further stop blood flow and accelerate the thrombolysis, in addition to preventing endoleak.

The skirt 20 includes an outer-layer radial supporting structure 21 and an outer-layer coating membrane 22 covering the outer-layer radial supporting structure. The self-expandable skirt 20 may be compressed and may expand in its radial direction. In one embodiment, the radial deformability of the radial supporting structure 21 of the skirt 20 is greater than that of a stent body of the tube body 10. The radial deformability is defined as: under the action of the same radial force, a greater radial length variation or a greater radial length change rate indicates higher radial deformability and lower radial supportability of the radial supporting structure, and on the contrary, a lesser radial length variation or a lesser radial length change rate indicates lower radial deformability and higher radial supportability. In other words, under the condition of the same radial change rate or the same radial variation, a radial external force required by the outer-layer radial supporting structure 21 of the skirt 20 is greater than that required by the stent body of the tube body 10, which indicates that the outer-layer radial supporting structure 21 is relatively low in radial deformability and relatively high in radial supportability; please refer to CN105496603A for more details. In other possible embodiments, the skirt 20 may also include only the coating membrane. A gap between the tube body 10 and a blood vessel is filled with the soft coating membrane so as to prevent the endoleak. The outer-layer radial supporting structure 21 provides the skirt 20 with a radial expandability which also may be called the radial supportability or radial supporting force. For example, the radial supporting structure may be made of a memory alloy material (such as a nickel-titanium alloy) so as to be self-expandable. The outer-layer radial supporting structure 21 may have multiple turns of waveform ring-like objects arrayed along the axial direction, or may be a mesh structure woven from a metal wire, or may be a cut mesh structure that is cut from a metal tube. Those ordinarily skilled in the art can select proper radial supporting structures as required, so no more details will be provided here.

The skirt 20 has an open end and a closed end. The open end has a column shape, and the closed end has a cone shape connected with a column. The closed end is hermetically connected with the surface of the tube body 10 so as to divide the tube body 10 into a first tube body 11 encircled by the skirt 20 and located on one side of the closed end, and a second tube body 12 located on the other side of the closed end. The open end of the skirt 20 extends towards a direction away from the second tube body 12, and the extending direction of the second tube body 12 is opposite to that of the skirt 20. When the luminal stent is compressed, the skirt 20 encircles the peripheral surface of the first tube body 11. Due to its radial supporting structure 21, the skirt 20 may be adhered to the inner wall of a lumen after the stent is implanted, and an effective gap is formed between the skirt 20 and the first tube body 11. Blood would flow into the gap when flowing into the luminal stent from the proximal end.

As the orifice at the closed end is closed, the blood flowing into the gap will be stopped so as to reduce and even avoid the blood flow from flowing into the gap formed between the second tube body 12 and the inner wall of the lumen, and to cut off a channel or an opening of a type-I endoleak. In addition, this part of the blood would be directly thrombosed in the gap to produce a better sealing and filling effect. In this sealing process, a sealing effect may be achieved only by use of the inflow blood in the normal blood circulation without adding other sealing or filling materials into the luminal stent in advance or after implantation of the luminal stent, so that no extra biological risk caused by the sealing or filling material would occur. In other possible embodiments of the present application, the skirt 20 may have a cone shape, excluding the column connected with the cone as shown in FIG. 4.

In the present embodiment, the thickness of the outer-layer coating membrane 22 of the skirt 20 is 0.01 to 0.05 mm, and the wire diameter of the outer-layer radial supporting structure 21 is 0.003 to 0.006 inch (0.0762 to 0.1534 mm). The thickness of the outer-layer coating membrane 20 is less than that of the coating membrane of the tube body 10, and the wire diameter of the outer-layer radial supporting structure 21 is less than that of the radial supporting structure of the tube body 10.

In addition, in other possible embodiments, both ends of the skirt are hermetically connected with the tube body. The skirt with the two closed ends may only include the coating membrane, or may further include the above-mentioned radial supporting structure.

Figure 7:
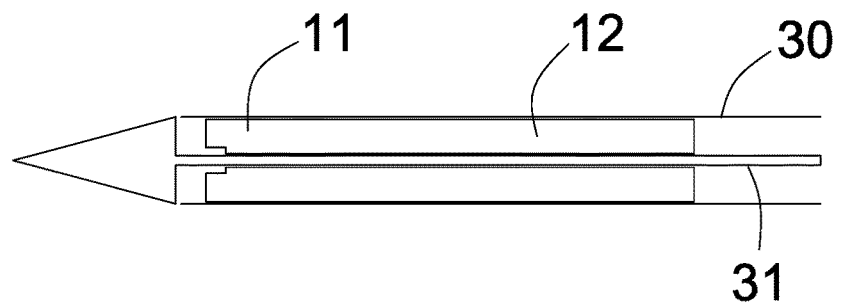
FIG. 7 is a structural schematic diagram of the luminal stent in FIG. 4 in a compressed state in a sheath.

In the embodiment as shown in the figures, the second tube body 12 includes a tapered section 121 connected with the first tube body 11, and a straight barrel section 122 connected with the tapered section 121. The end that is closest to the first tube body 11 of the tapered section 121 has the same diameter as the part that is encircled by the skirt 20 of the first tube body. In addition, the end that is away from the first tube body 11 of the tapered section 121 has the same diameter as that of the straight barrel section 122. The diameter of the tapered section 121 is gradually increased from the end closest to the first tube body 11 to the end closest to the straight barrel section 122. In one embodiment, the axial length of the tapered section 121 is 5 to 10 mm. In other words, the length of the tapered section 121 along the longitudinal center axis of the tube body is 5 to 10 mm. The diameter of the straight barrel section 122 is greater than that of the part that is encircled by the skirt 20 of the first tube body 11, and the axial length of the straight barrel section 122 is greater than that of the first tube body 11. In one embodiment, in a natural expanded state, the difference between the diameter of the straight barrel section 122 and the diameter of the part encircled by the skirt 20 of the first tube body 11 is no more than 8 mm, and the compression diameters of the first tube body 11 and the second tube body 12 are slightly different, so that after the luminal stent is compressed into the sheath, the contact force between the first tube body 11 and a sheath core 31, as well as the contact force between the second tube body 12 and the sheath core 31, are increased. In one embodiment, in the natural state, the ratio of the difference between the diameter of the straight barrel section 122 and the diameter of the part encircled by the skirt 20 of the first tube body 11 to the diameter of the straight barrel section 122 is 0.1 to 0.2. In actual use, the oversized region of the straight barrel section 122 of the second tube body 12 is [10%, 20%], namely the radial length of the second tube body 12 may be generally compressed by 10 to 20 percent after the second tube body 12 is implanted into the blood vessel to maintain a relatively high anchoring force between the straight barrel section 122 of the second tube body 12 and the blood vessel wall, so that during the implantation into the blood vessel, the difference between the diameter of the first tube body 11 and the diameter of the straight barrel section 122 of the second tube body 12 is relatively small, and the blood flow volumes of the first tube body 11 and the second tube body 12 may be kept consistent, which avoids the problem of turbulent flow in a connecting section due to inconsistent tube diameters of the first tube body 11 and the second tube body 12. In the present application, it is defined that when the first tube body 11, the second tube body 12, and the skirt 20 encircling the periphery of the first tube body 11 are compressed to the extreme limit by a radial force distributed along the circumferential direction uniformly of the luminal stent, their outer diameters are compression diameters, as shown in FIG. 7. The maximum compression diameters of the skirt 20 and the first tube body 11 encircled by the skirt 20 are approximately equal to the maximum compression diameter of the second tube body 12. In one embodiment, an absolute value of the difference between the maximum compression diameters of the skirt 20 together with the first tube body 11 encircled by the skirt 20 and the maximum compression diameter of the second tube body 12 is no more than 0.1 mm. The lesser the difference, the better. When the difference is close to 0, the luminal stent compressed into the sheath is an equal-diameter column, which means that the contact force between the luminal stent and the sheath core is uniform. It is worth noting that in the present embodiment, the tube body 10 is a column having a uniform tube diameter, so that its maximum compression diameter is the compression diameter. In other embodiments, if the tube diameter of the tube body 10 is not uniform, the compression diameter of a part having the maximum diameter shall be the maximum compression diameter.

Figure 5:
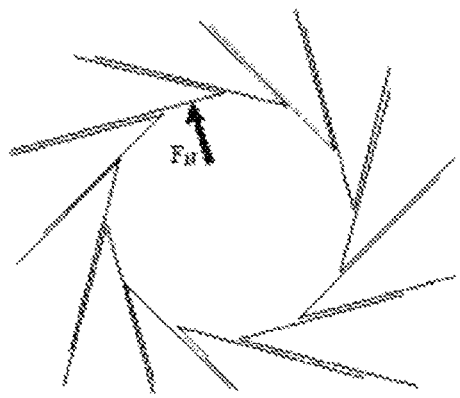
FIG. 5 is a structural schematic diagram of a force application part of a radial force tester of the present application.
Figure 6:
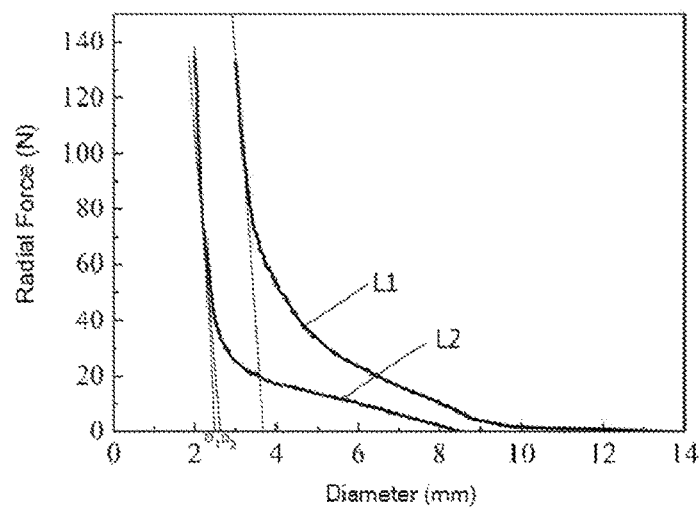
FIG. 6 is a compression curve chart of a first tube body and a second tube body in the first embodiment of the luminal stent of the present application.

Specifically, the compression diameter may be tested through the radial force. A functional relation between the compression diameter and the radial force is obtained by using a computer. When the compression amount is at a maximum, the increase of the force has little impact on the change of the compression amount, so that a curve of a stable increased force is obtained through computer fitting. Specifically, the sheath core, which is preferably a hard sheath core of a regular size, extends through the luminal stent, and the changing speed of the outer diameter of a force application part, as shown in FIG. 5, of a radial force tester is set at 0.1 mm/s until the sheath core is in close contact with the luminal stent. A series of discrete values can be obtained through the test method, and are connected into a relation curve of the radial force and the compression value, as shown in FIG. 6, wherein the X axis represents the compression diameter, and the Y axis represents the applied radial force. The compression curve L2 of the first tube body 11 is taken for example. Tangent lines of discrete points are respectively made on the compression curve L2 to obtain a plurality of intersections between the tangent lines and the X axis, and two points D1 and D2 are selected from these intersections. If the absolute value of the difference value between the two points D1 and D2 is not more than 0.01, it is defined in D1 and D2 that D1 is the compression diameter of the first tube body 11. As shown in FIG. 7, before being implanted into the blood vessel, the luminal stent is required to be compressed into the sheath 30 at first, and the sheath core 31 is enabled to extend through the luminal stent. As the diameter of the part encircled by the skirt 20 of the first tube body 11 is less than that of the second tube body 12, the compression diameters of the completely compressed skirt 20 and the completely compressed first tube body 11 encircled by the skirt 20 are basically equal to the compression diameter of the second tube body 12.

The diameter of the second tube body of the luminal stent of the present application is greater than that of the first tube body, so that the second tube body is in closer contact with the sheath core after the luminal stent is compressed into the sheath. Furthermore, after compression, the maximum compression diameter of the second tube body is approximately equal to that of the first tube body encircled by the skirt, so that a contact force of the luminal stent with the sheath core in the sheath is more uniform, which may prevent the luminal stent from sliding during the release process and avoid the risk caused by the displacement of the luminal stent.

It can be understood that when the first tube body 11 has a part not encircled by the skirt 20 and this part has a relatively short axial length (generally not more than 2 cm), sliding of this part relative to the sheath core would not occur even though the diameter of this part is not greater than that of the part encircled by the skirt. When the first tube body 11 has a relatively long part not encircled by the skirt, the diameter of this part may be designed to be greater than that of the part encircled by the skirt of the first tube body.

In the embodiment as shown in the figures, the first tube body includes a first coating membrane and a first radial supporting structure connected with the first coating membrane. The second tube body includes a second coating membrane and a second radial supporting structure connected with the second coating membrane. The first radial supporting structure includes multiple first waveform ring-like objects arrayed in sequence, and the second radial supporting structure includes multiple second waveform ring-like objects arrayed in sequence. The thickness of the first coating membrane is equal to that of the second coating membrane, and the wire diameters of the first waveform ring-like objects are equal.

Second Embodiment

Figure 8:
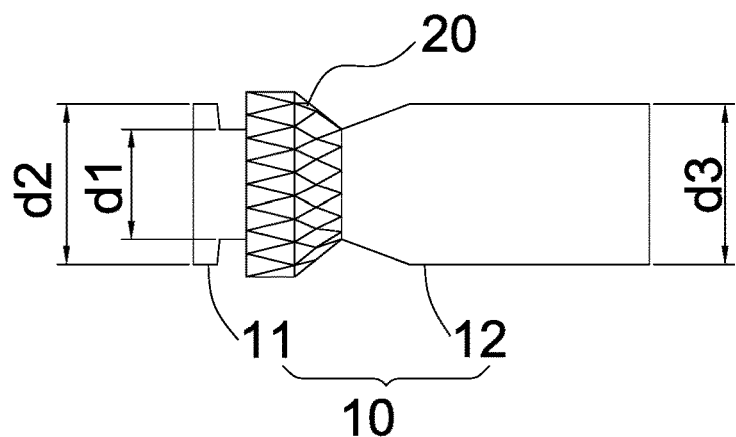
FIG. 8 is a structural schematic diagram of a second embodiment of a luminal stent of the present application shown in an expanded state.
Figure 9:
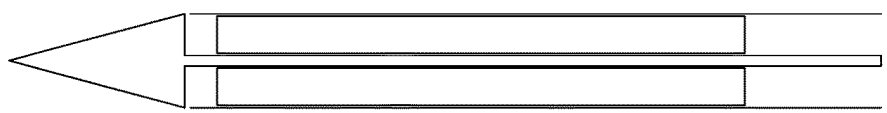
FIG. 9 is a structural schematic diagram of the luminal stent of FIG. 8 in a compressed state in a sheath.

As shown in FIG. 8, the luminal stent structure of the present embodiment is basically the same as that of the first embodiment. The difference lies in that in the present embodiment, the first tube body 11 in an expanded state has a varying diameter along its axial direction, and the second tube body 12 is of a straight barrel shape, namely any two points along the axial direction have the same in diameter d3. Specifically, the part encircled by the skirt 20 of the first tube body 11 has a first maximum diameter d1, and the part not encircled by the skirt 20 of the first tube body 11 has a second maximum diameter d2, with d1<d2=d3. In other words, the cross section of the first tube body 11 has a stepped shape. As shown in FIG. 9, due to the step-like structure of the first tube body 11, in a compressed state of the luminal stent, the skirt 20 is completely compressed into the part having the first diameter d1, and the compression diameter of the part encircled by the skirt 20 is equal to d2 and d3.

The part having the relatively large diameter d2 is located at a position away from the skirt 20, and this position is an inlet end of the blood flow. The relatively large diameter d2 may allow a contact area between the first tube body 11 and the blood to be larger, and allow blood to flow into the first tube body 11 more easily. It is worth noting that the diameters of the first tube body 11 and the second tube body 12 also may vary in various ways along their axial directions. For example, the diameter of the first tube body 11 may be gradually decreased along a direction close to a joint of the skirt 20 and the tube body 10.

Third Embodiment

Figure 10:
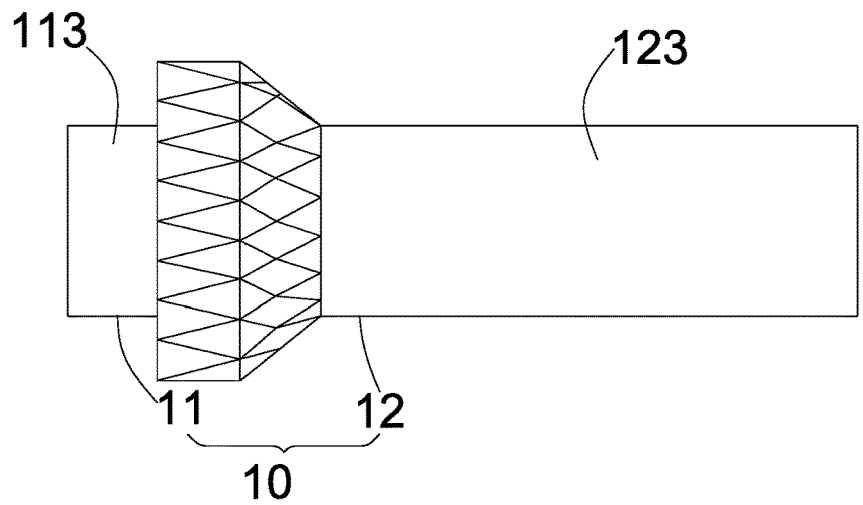
FIG. 10 is a structural schematic diagram of a third embodiment of a luminal stent of the present application shown in an expanded state.

As shown in FIG. 10, the luminal stent structure of the present embodiment is basically the same as that of the first embodiment. The difference lies in that in the present embodiment, the first tube body 11 and the second tube body 12 are the same in diameter. Specifically, the thickness of the first coating membrane 113 of the first tube body 11 is less than that of the second coating membrane 123 of the second tube body 12. In one embodiment, a ratio of the thickness of the second coating membrane 123 to the thickness of the first coating membrane 113 is 1.2-4.5. Of course, the ratio of the thickness of the second coating membrane to the thickness of the first coating membrane may be adjusted according to the structure of the skirt so as to keep the compression diameter of the luminal stent basically consistent.

Figure 11:
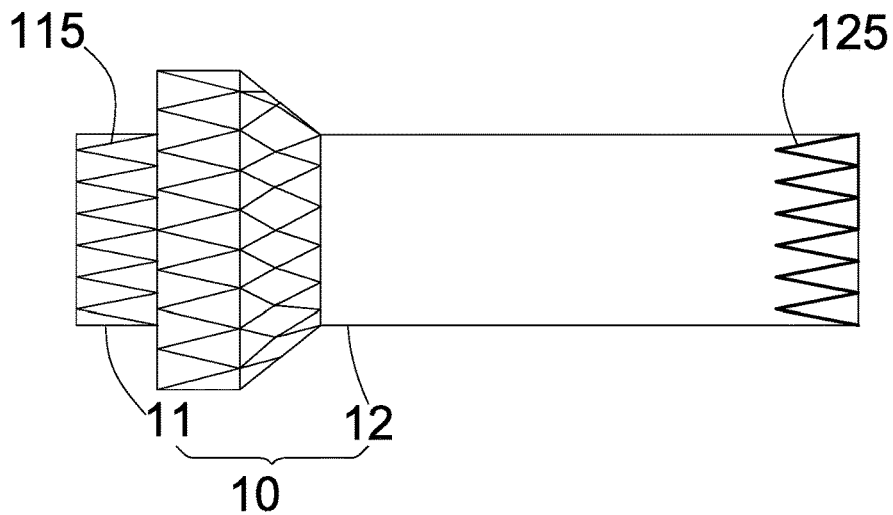
FIG. 11 is a structural schematic diagram of a fourth embodiment of a luminal stent of the present application shown in an expanded state.
Figure 12:
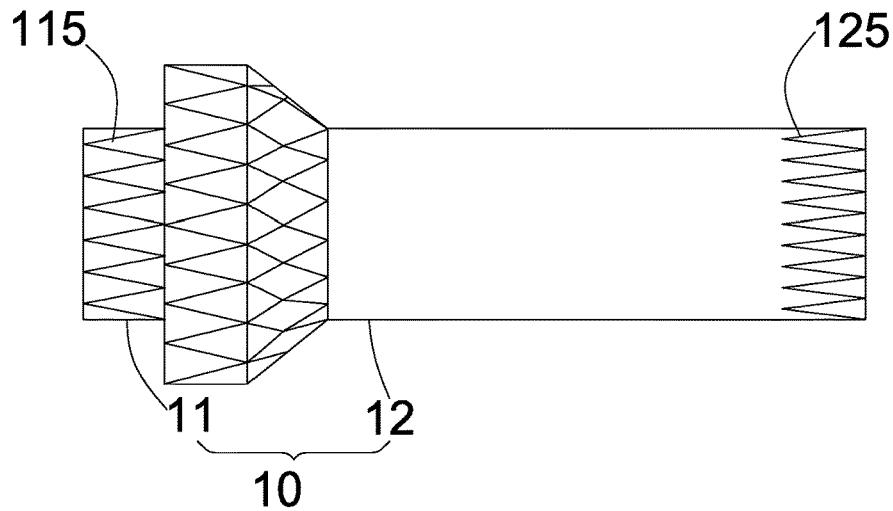
FIG. 12 is a structural schematic diagram of a fifth embodiment of a luminal stent of the present application shown in an expanded state.

It can be further understood that the metal coverage rate of the first radial supporting structure of the first tube body 11 is greater than that of the second tube body 12. For example, as shown in FIG. 11, the wire diameter of the first waveform ring-like object 115 is greater than that of the second waveform ring-like object 125. Specifically, both the first waveform ring-like object 115 and the second waveform ring-like object 125 include the same number of wave crests and have equal wave heights. The ratio of the wire diameter of the second waveform ring-like object 125 to the wire diameter of the first waveform ring-like object 115 is 2.0-5.0 so as to enable the compression diameters of all parts of the luminal stent to be approximately the same. For another example, as shown in FIG. 12, the number of the wave crests of the first waveform ring-like object 115 is less than that of the wave crests of the second waveform ring-like object 125. Specifically, the first waveform ring-like object 115 and the second waveform ring-like object 125 adopt the same wire diameters and equal wave heights, and a ratio of the number of the wave crests of the second waveform ring-like object 125 to the number of the wave crests of the first waveform ring-like object 115 is 4-23. It can be further understood that the thickness of the first coating membrane and the metal coverage rate of the first radial supporting structure of the first tube body and the thickness of the second coating membrane and the metal coverage rate of the second radial supporting structure of the second tube body also may be adjusted simultaneously according to a desired clinical situation, so as to ensure that the compression diameters of all the parts of the luminal stent are approximately equal.

It should be further noted that all the above-mentioned embodiments may also be combined with one another under certain conditions. For example, in the embodiment 1, according to an actual condition, when the diameter of the first tube body is less than that of the second tube body, the thickness of the first coating membrane and the metal coverage rate of the first radial supporting structure of the first tube body and the thickness of the second coating membrane and the metal coverage rate of the second radial supporting structure of the second tube body also may be further adjusted, so as to ensure that the compression diameters of all the parts of the luminal stent are approximately equal.

The above-mentioned embodiments are merely expressive of several implementation modes of the present application, and descriptions are relatively specific and detailed, but cannot be understood as limitations to the patent scope of the present application. It should be noted that those ordinarily skilled in the art can further make a plurality of transformations and improvements without departing from the concept of the present application, and these transformations and improvements shall all fall within the protection scope of the present application. Therefore, the protection scope of the patent of the present application shall be based on attached claims.

The invention claimed is:

1. A luminal stent, comprising:
a tube body that can be compressed and expanded in the radial direction; and
an anti-leakage structure connected with the tube body, wherein the tube body is divided by the anti-leakage structure into a first tube body located on one side of the anti-leakage structure and a second tube body located on the other side of the anti-leakage structure; at least part of the first tube body is encircled by the anti-leakage structure; and
wherein the anti-leakage structure has an open end and a closed end, the anti-leakage structure is configured as a skirt with a greater diameter at the open end, and wherein the closed end is located at a joint of the first tube body and the second tube body; and
wherein the first tube body comprises a first coating membrane and a first radial supporting structure connected with the first coating membrane; the second tube body comprises a second coating membrane connected with the first coating membrane and a second radial supporting structure connected with the second coating membrane; the thickness of the first coating membrane is less than that of the second coating membrane.

2. The luminal stent according to claim 1, wherein the first radial supporting structure comprises multiple first waveform ring-like objects arrayed in sequence, and the second radial supporting structure comprises multiple second waveform ring-like objects arrayed in sequence; the wire diameter of each first waveform ring-like object is less than that of each second waveform ring-like object.

3. The luminal stent according to claim 2, wherein the ratio of the wire diameter of each second waveform ring-like object to the wire diameter of each first waveform ring-like object is 2.0-5.0.

4. The luminal stent according to claim 1, wherein the second tube body comprises a tapered section connected with the first tube body and a straight barrel section connected with the tapered section; and the diameter of the straight barrel section is greater than that of the part encircled by the anti-leakage structure of the first tube body.

5. The luminal stent according to claim 4, wherein the difference between the diameter of the straight barrel section and the diameter of the part encircled by the anti-leakage structure of the first tube body is no more than 8 mm.

6. The luminal stent according to claim 5, wherein a ratio of the difference between the diameter of the straight barrel section and the diameter of the part encircled by the anti-leakage structure of the first tube body to the diameter of the straight barrel section is 0.1-0.2.

7. The luminal stent according to claim 1, wherein a part encircled by the anti-leakage structure of the first tube body has a first diameter, and a part not encircled by the anti-leakage structure of the first tube body has a second diameter; with the second diameter being unequal to the first diameter, and the second diameter being greater than the first diameter.

8. The luminal stent according to claim 1, wherein the anti-leakage structure comprises an outer-layer coating membrane and an outer-layer radial supporting structure connected with the outer-layer coating membrane.

9. The luminal stent according to claim 1, wherein the metal coverage rate of the first radial supporting structure is greater than that of the second radial supporting structure.

10. The luminal stent according to claim 9, wherein the first radial supporting structure comprises multiple first waveform ring-like objects arrayed in sequence, and the second radial supporting structure comprises multiple second waveform ring-like objects arrayed in sequence; the wire diameter of each first waveform ring-like object is less than that of each second waveform ring-like object, and/or, the number of wave crests of each first waveform ring-like object is less than that of wave crests of each second waveform ring-like object.

11. A luminal stent, comprising:
a tube body that can be compressed and expanded in the radial direction; and
an anti-leakage structure connected with the tube body, wherein the tube body is divided by the anti-leakage structure into a first tube body located on one side of the anti-leakage structure and a second tube body located on the other side of the anti-leakage structure; at least part of the first tube body is encircled by the anti-leakage structure; in a compressed state, the second tube body and the anti-leakage structure together with the first tube body encircled by the anti-leakage structure have maximum compression diameters when compressed to the extreme limit by a radial force distributed uniformly along a circumferential direction of the luminal stent; and the maximum compression diameters of the anti-leakage structure together with the first tube body encircled by the anti-leakage structure are approximately equal to the maximum compression diameter of the second tube body;
wherein the first tube body comprises a first coating membrane and a first radial supporting structure connected with the first coating membrane; the second tube body comprises a second coating membrane connected with the first coating membrane and a second radial supporting structure connected with the second coating membrane; the thickness of the first coating membrane is less than that of the second coating membrane, and/or, the metal coverage rate of the first radial supporting structure is greater than that of the second radial supporting structure; and
wherein the ratio of the thickness of the second coating membrane to the thickness of the first coating membrane is 1.2-4.5.

12. A luminal stent, comprising:
a tube body that can be compressed and expanded in the radial direction; and
an anti-leakage structure connected with the tube body, wherein the tube body is divided by the anti-leakage structure into a first tube body located on one side of the anti-leakage structure and a second tube body located on the other side of the anti-leakage structure; at least part of the first tube body is encircled by the anti-leakage structure; and
wherein the anti-leakage structure has an open end and a closed end, the anti-leakage structure is configured as a skirt with a greater diameter at the open end, and wherein the closed end is located at a joint of the first tube body and the second tube body, the skirt has a column that extends from the open end, and a cone shape connecting the column with the closed end; and wherein the second tube body comprises a tapered section connected with the first tube body and a straight barrel section connected with the tapered section; and the diameter of the straight barrel section is greater than that of the part encircled by the anti-leakage structure of the first tube body.

13. The luminal stent according to claim 12, wherein in a compressed state, the second tube body and the anti-leakage structure together with the first tube body encircled by the anti-leakage structure have maximum compression diameters when compressed to the extreme limit by a radial force distributed uniformly along a circumferential direction of the luminal stent; and an absolute value of the difference between the maximum compression diameters of the anti-leakage structure together with a part encircled by the anti-leakage structure of the first tube body, and the maximum compression diameter of the second tube body, is no more than 0.1 mm.

14. The luminal stent according to claim 12, wherein the first tube body comprises a first radial supporting structure and the second tube body comprises a second radial supporting structure, wherein the metal coverage rate of the first radial supporting structure is greater than that of the second radial supporting structure.

15. The luminal stent according to claim 12, wherein the difference between the diameter of the straight barrel section and the diameter of the part encircled by the anti-leakage structure of the first tube body is no more than 8 mm.

16. The luminal stent according to claim 15, wherein a ratio of the difference between the diameter of the straight barrel section and the diameter of the part encircled by the anti-leakage structure of the first tube body to the diameter of the straight barrel section is 0.1-0.2.

17. The luminal stent according to claim 12, wherein the axial length of the tapered section is 5 to 10 mm.

18. The luminal stent according to claim 12, wherein the anti-leakage structure comprises an outer-layer coating membrane and an outer-layer radial supporting structure connected with the outer-layer coating membrane.

19. The luminal stent according to claim 12, wherein the first tube body comprises a first radial supporting structure and the second tube body comprises a second radial supporting structure, wherein the first radial supporting structure comprises multiple first waveform ring-like objects arrayed in sequence, and the second radial supporting structure comprises multiple second waveform ring-like objects arrayed in sequence; the wire diameter of each first waveform ring-like object is less than that of each second waveform ring-like object, and/or the number of wave crests of each first waveform ring-like object is less than that of wave crests of each second waveform ring-like object.

* * * * *